United States Patent
Cantwell et al.

(10) Patent No.: US 11,951,141 B2
(45) Date of Patent: Apr. 9, 2024

(54) REPLICATION-ENHANCED ONCOLYTIC ADENOVIRUSES

(71) Applicants: MEMGEN, Inc., Houston, TX (US); H. Lee Moffitt Cancer Center and Research Institute, Inc., Tampa, FL (US)

(72) Inventors: Mark J. Cantwell, Meadow Vista, CA (US); Amer A. Beg, Tampa, FL (US)

(73) Assignees: MEMGEN, INC., Houston, TX (US); H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 689 days.

(21) Appl. No.: 17/091,549

(22) Filed: Nov. 6, 2020

(65) Prior Publication Data
US 2021/0128653 A1    May 6, 2021

Related U.S. Application Data

(60) Provisional application No. 62/931,282, filed on Nov. 6, 2019.

(51) Int. Cl.
*A61K 35/761* (2015.01)
*A61P 35/00* (2006.01)
*C12N 7/00* (2006.01)
*C12N 15/113* (2010.01)
*C12N 15/12* (2006.01)
*C12N 15/22* (2006.01)

(52) U.S. Cl.
CPC ............ *A61K 35/761* (2013.01); *A61P 35/00* (2018.01); *C12N 7/00* (2013.01); *C12N 2710/10021* (2013.01); *C12N 2710/10032* (2013.01); *C12N 2710/10043* (2013.01); *C12N 2710/10071* (2013.01); *C12N 2830/00* (2013.01)

(58) Field of Classification Search
None
See application file for complete search history.

(56) References Cited

U.S. PATENT DOCUMENTS

| | | | | |
|---|---|---|---|---|
| 2013/0323205 | A1* | 12/2013 | Diaconu | A61P 35/02 435/456 |
| 2018/0369404 | A1* | 12/2018 | Larson | A61K 35/761 |
| 2021/0252135 | A1* | 8/2021 | Coffin | A61P 35/00 |

OTHER PUBLICATIONS

Zheng et al, Combination IFNb and Membrane-Stable CD40L Maximize Tumor Dendritic Cell Activation and Lymph Node Trafficking to Elicit Systemic T-cell Immunity, Cancer Immunol Res 2023;11:466-85.*

Diaconu et al., Immune Response Is an Important Aspect of the Antitumor Effect Produced by a CD40L-Encoding Oncolytic Adenovirus, Cancer Res; 72(9) May 1, 2012, 2327-2338.*

* cited by examiner

*Primary Examiner* — Maria Marvich
(74) *Attorney, Agent, or Firm* — Jackson Walker LLP; Leisa Talbert Peschel

(57) ABSTRACT

Disclosed are replication-enhanced oncolytic adenoviruses. These oncolytic adenoviruses have tumor-specific replication capable of enhanced tumor oncolysis and enhanced therapeutic transgene expression. Also disclosed are methods comprising administering a replication-enhanced oncolytic adenovirus for patients suffering from a cancer.

7 Claims, 19 Drawing Sheets

Specification includes a Sequence Listing.

REPLICATION-ENHANCED ONCOLYTIC ADENOVIRUSES

JOINT RESEARCH AGREEMENT

The present invention was made as a result of activities undertaken within the scope of a joint research agreement that was in effect at the time the present invention was made. The parties to said joint research agreement are Memgen, Inc. (formerly, Memgen, LLC) and H. Lee Moffitt Cancer Center and Research Institute, Inc.

BACKGROUND OF THE INVENTION

1. Field of the Invention

The invention generally relates to the field of oncolytic viruses and oncology. More specifically, the invention relates to compositions of oncolytic virus with enhanced viral replication in tumor cells for treating cancer.

2. Description of Related Art

Oncolytic viruses are a class of cancer therapeutic agents with a dual mechanism of action: 1) tumor cell killing through selective viral replication in tumor cells resulting in direct tumor lysis and 2) induction of systemic anti-tumor immunity by releasing antigens from destroyed tumor cells. Both native and genetically modified viruses are in development. The US FDA approved in 2015 the first oncolytic virus, talimogene laherparepvec (IMLYGIC®, Amgen Inc., Thousand Oaks, CA), a genetically modified herpesvirus encoding granulocyte-macrophage colony-stimulating factor (GM-CSF) for the local treatment of melanoma, as described by Kohlhapp et. al. 2016 Clinical Cancer Research. However, herpesvirus is only one of many oncolytic viruses under investigation regarding their oncolytic properties.

Oncolytic adenoviral vectors have been extensively used for cancer gene therapy for several reasons, including broad tropism for infection of multiple tumor types, vector stability, capability to manufacture and purify virus to high titers, transgene-carrying capacity, lack of integration into the host genome, and benign safety profiles.

Despite these desirable attributes of oncolytic adenovirus vectors, these vectors can also be limited in their use for cancer therapy for multiple reasons, including non-specific infection and replication in normal cells, slow or low viral replication rates, vector clearance and neutralization as a result of anti-adenovirus immunogenicity, and low oncolytic capacity. These limitations can also contribute to inefficient gene transfer or expression when used as a delivery vehicle.

Efforts have been aimed at improving replication-competent adenoviruses to address its limitations. These efforts include modifications of adenovirus genome components to impart selective replication in tumor cells. Well characterized modifications include a 24 base pair deletion of the adenovirus E1A gene (delta-24 E1A), deletion of the E1B 55K viral gene, and even substitution of viral promoters such as E1A with tumor-associated-antigen promoters like the alpha-feto-protein promoter or prostate antigen promoter.

Despite these examples of selective tumor targeting, the prior art is deficient in recombinant adenovirus vectors that replicate at substantially improved rates or levels in tumor cells.

Accordingly, there remains a need for oncolytic viral vectors that improve one of its primary mechanisms of action: selectively enhanced viral replication in tumor cells resulting in improved tumor lysis. The present invention addresses this need for oncolytic adenovirus vectors with enhanced viral replication in tumors cells, improved tumor lysis, and improved therapeutic transgene expression.

All of the subject matter discussed in the Background is not necessarily prior art and should not be assumed to be prior art merely as a result of its discussion in the Background section. Along these lines, any recognition of problems in the prior art discussed in the Background or associated with such subject matter should not be treated as prior art unless expressly stated to be prior art. Instead, the discussion of any subject matter in the Background should be treated as part of the inventor's approach to the particular problem, which in and of itself, may also be inventive.

SUMMARY OF THE INVENTION

The following presents a simplified summary of the disclosure in order to provide a basic understanding of some aspects of the disclosure. This summary is not an exhaustive overview of the disclosure. It is not intended to identify key or critical elements of the disclosure or to delineate the scope of the disclosure. Its sole purpose is to present some concepts in a simplified form as a prelude to the more detailed description that is discussed later.

We have surprisingly found that insertion of two exogenous promoter/enhancer elements (a CMV promoter/enhancer and a SV40 early promoter/enhancer) in the adenovirus genome, together with previously described modifications of adenovirus E1A, E1B, and E3 gene components, leads to dramatically enhanced viral replication in tumor cells and enhanced tumor oncolysis. We also surprisingly found this newly described recombinant adenovirus can act as a vehicle for delivery of one or more therapeutic transgenes to effect dramatically enhanced expression of these transgenes in tumor cells. While use of either the CMV promoter/enhancer or the SV40 promoter/enhancer by themselves have been used individually in generating recombinant oncolytic adenoviruses, we are not aware of any prior art describing the dual use of the promoters in an oncolytic virus, and are not aware of prior art describing our unexpected finding this dual promoter oncolytic adenovirus would lead to enhanced tumor-specific viral replication.

In some embodiments, the present disclosure relates to an oncolytic adenovirus with viral genome modifications that impart enhanced virus replication.

In some embodiments, the recombinant oncolytic adenovirus contains both a CMV promoter/enhancer and a SV40 promoter/enhancer inserted in the viral genome.

In some embodiments, the recombinant oncolytic adenovirus contains both a CMV promoter/enhancer and a SV40 promoter/enhancer inserted in the viral genome, possesses a deletion in part or all of the E3 coding region, possesses a E1A gene comprising a delta-24 deletion, and includes a E1B 55K deletion.

In preferred embodiments, the recombinant oncolytic adenovirus contains a CMV promoter/enhancer inserted in a noncoding region upstream of the adenovirus E1coding region, contains a SV40 promoter/enhancer inserted in the adenovirus E3 region, possesses a deletion in part or all of the E3 coding region, and possesses a E1A gene comprising a delta-24 deletion; and includes a E1B 55K deletion.

Further embodiments of the invention include heterologous nucleic acid sequences encoding one or more therapeutic proteins.

In some embodiments, the present disclosure provides for an oncolytic adenovirus with enhanced virus replication specific for tumor cells In further embodiments, the invention provides methods of treating a malignancy, preferably cancer, by administration of the replication-enhanced recombination oncolytic adenovirus.

The details of one or more embodiments are set forth in the description below. The features illustrated or described in connection with one exemplary embodiment may be combined with the features of other embodiments. Thus, any of the various embodiments described herein can be combined to provide further embodiments. Aspects of the embodiments can be modified, if necessary, to employ concepts of the various patents, applications, and publications as identified herein to provide yet further embodiments. Other features, objects, and advantages will be apparent from the description, the drawings, and the claims.

BRIEF DESCRIPTION OF THE DRAWINGS

The disclosure may be understood by reference to the following description taken in conjunction with the accompanying drawings, in which.

BRIEF DESCRIPTION OF THE SEQUENCES

Figure 1:
FIG. 1 schematically shows a replication-enhanced oncolytic adenovirus possessing a CMV promoter/enhancer and a SV40 promoter/enhancer inserted in the adenovirus genome; and regions for insertion of heterologous nucleic acids for expression of one or more therapeutic protein(s).

SEQ ID NO: 1 shows the nucleotide sequence of the CMV promoter/enhancer inserted between the left inverted terminal repeat (ITR) and 5'-end of the functional E1A region.

SEQ ID NO: 2 shows the nucleotide sequence of the SV40 early promoter/enhancer inserted between the E3 12.5K and E3 RID-alpha regions.

DETAILED DESCRIPTION OF THE INVENTION

Various illustrative embodiments of the disclosure are described below.

In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

While the subject matter disclosed herein is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

Adenovirus

"Adenovirus" (Ad) is a large (approximately 36 kb) DNA virus that infects humans, but which also display a broad host range. Physically, adenovirus is an icosahedral virus containing a double-stranded, linear DNA genome. There are approximately 57 serotypes of human adenoviruses, which are divided into six families based on molecular, immunological, and functional criteria. By adulthood, virtually every human has been infected with the more common adenovirus serotypes, the major effect being cold-like symptoms.

Adenoviral infection of host cells results in adenoviral DNA being maintained episomally, which reduces the potential genotoxicity associated with integrating vectors. In addition, adenoviruses are structurally stable, and no genome rearrangement has been detected after extensive amplification. Adenovirus can infect most epithelial cells regardless of their cell cycle stage. So far, adenoviral infection appears to be linked only to mild disease such as acute respiratory disease in humans.

Oncolytic Adenovirus

There are a broad range of oncolytic virus types in development as anti-cancer agents, including adenovirus (see Russell et al., 2014 Nature Biotechnology and Lawler et al, 2017 JAMA Oncology).

Multiple biologic properties may be considered in selection or design of a therapeutic oncolytic adenovirus for desired therapeutic activity, including: selective targeting of cancer cells for infection through natural tropism of cell surface proteins or by engineering adenovirus to directly target cancer cells; selective replication in cancer cells; attenuation of viral pathogenesis; enhancing lytic activity; modification of the antiviral immune response that can lead to rapid clearance of adenovirus; and modification of systemic anti-tumor immunity through genetic modification of adenoviruses to incorporate cytokines, immune agonists, or immune checkpoint blockers.

Replication competent oncolytic adenovirus vectors have several properties that make them ideal for therapeutic applications, including infectivity of a broad range of cell and tumor types, infection of non-dividing cells, lack of genomic integration, high titers, capacity to carry transgenes, in vitro and in vivo stability, and expression of transgenes. Adenovirus expression vectors include constructs containing adenovirus sequences sufficient to (a) support packaging of the construct and (b) to ultimately express a recombinant gene construct that has been cloned therein if desired.

Modulation of the biological properties of oncolytic adenoviruses can impact a range of immune interactions that may be beneficial or detrimental in effect on cancer treatment. The interactions depend on the specific tumor, the site and extent of the disease, the immunosuppressive tumor microenvironment, the oncolytic virus platform, the dose, time, and delivery conditions, as well as individual patient responses (see generally Aurelian L., "Oncolytic viruses as immunotherapy: progress and remaining challenges," Onco. Targets Ther. 2016, 9:2627-2637). For example, the presence of adenovirus E3 genes has been reported to increase the oncolytic potency of conditionally replicating adenovirus in vitro and in vivo (see Suzuki K, Alemany R, Yamamoto M, and Curiel D T, "The presence of the adenovirus E3 region improves the oncolytic potency of conditionally replicative adenoviruses" Clin. Cancer Res. 2002 Nov., 8(11):3348-59). In particular, the E3-11.6 kDa Adenovirus Death Protein (ADP) is thought to be required for efficient cell death (see Tollefson A, Ryerse J, and Scaria A, et al. "The E3-11.6-kDa Adenovirus Death Protein (ADP) is Required for Efficient Cell Death: Characterization of Cells Infected with adp Mutants," Virology 1996, 220:152-162).

Despite these aforementioned advancements, the prior art is relatively deficient in adenovirus vectors that replicate at substantially improved rates or levels in tumor cells to effect one of an oncolytic adenovirus' primary mechanisms of action: viral replication leading to tumor lysis. Accordingly, there remains a need for oncolytic viral vectors that improve this primary mechanism of action: selectively enhanced viral replication in tumor cells resulting in improved tumor lysis.

Figure 2:
FIG. 2 schematically shows a replication-enhanced oncolytic adenovirus possessing a CMV promoter/enhancer inserted in a noncoding region upstream of the adenovirus E1 coding region, a SV40 promoter/enhancer inserted in the adenovirus E3 region, additional viral genome modifications, and regions for insertion of heterologous nucleic acids for expression of one or more therapeutic protein(s).

The present disclosure provides such oncolytic adenoviruses. We have surprisingly found that insertion of two exogenous promoters/enhancer elements (a CMV promoter/enhancer and a SV40 promoter/enhancer) at defined locations of the adenovirus genome, together with previously described modifications of adenovirus E1A, E1B, and E3 gene components, leads to dramatically enhanced viral replication in tumor cells and enhanced tumor oncolysis (FIG. 2).

We also surprisingly found this newly described recombinant adenovirus can act as an ideal vehicle for delivery of one or more therapeutic transgenes to effect enhanced expression of these transgenes in tumor cells. Members of any of the 57 human adenovirus serotypes (HAdV-1 to 57) may incorporate heterologous nucleic acid encoding therapeutic protein(s). Human Ad5 is well characterized genetically and biochemically (GenBank M73260; AC 000008). Thus, in a particular embodiment, the oncolytic adenovirus is a replication competent Ad5 serotype or a hybrid serotype comprising an Ad5 component. Within some embodiments of the disclosure, one or more heterologous sequences can be incorporated into a nonessential region of the adenovirus. Within some embodiments of the disclosure one or more heterologous sequences can be integrated downstream of the CMV promoter/enhancer and/or downstream of the SV40 promoter/enhancer. Representative examples of therapeutic proteins encoded by these heterologous genes include cytokines, chemokines, antibodies, and checkpoint inhibitors.

Promoter/Enhancers

Many promoters function with heterologous enhancer elements separated by DNA. CMV and SV40 "promoters" described here constitute both enhancer and promoter elements. The enhancer in CMV and SV40 "promoters" may function to increase expression of adenovirus genes promoters in a manner typical of enhancer action, and this may represent a mechanism of increase in replication.

Heterologous nucleic acid expression may be under the control of a promoter functional in mammalian cells, preferably human tumor cells. In one embodiment, the promoter directing expression of a heterologous nucleic acid encoding a therapeutic protein(s) is a cytomegalovirus (CMV) promoter/enhancer. In a further embodiment, the promoter directing expression of a heterologous nucleic acid encoding a therapeutic protein(s) is a SV40 promoter/enhancer.

The present invention provided herein comprises two promoters/enhancers with the ability to drive expression of heterologous nucleic acids encoding protein(s). A promoter generally comprises a sequence that functions to position the start site for RNA synthesis. The best example of this is the TATA box, but in some promoters lacking a TATA box, such as the promoter for the mammalian terminal deoxynucleotidyl transferase gene and the promoter for the SV40 early genes (a preferred embodiment of this current invention), a discrete element overlying the start site itself helps to fix the place of initiation. Additional promoter elements regulate the frequency of transcriptional initiation. These are typically in the region 30 to 110 bp upstream of the start site, although promoters have been shown to contain functional elements downstream of the start site as well. To bring a coding sequence "under the control of" a promoter, one positions the 5-prime end of the transcription initiation site of the transcriptional reading frame "downstream" of (i.e., 3-prime of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence. In preferred embodiments of the invention the CMV promoter incorporated in the replication-enhanced adenovirus is used in conjunction with a CMV enhancer region. In further preferred embodiments of the invention the SV40 promoter incorporated in the replication-enhanced adenovirus is used in conjunction with a SV40 enhancer region.

A promoter may be naturally associated with a nucleic acid sequence and obtained by isolating the 5-prime non-coding sequences located upstream of the coding segment and/or exon. Such a promoter can be referred to as "endogenous." Similarly, an enhancer may be naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other adenovirus, or prokaryotic or eukaryotic cell, and promoters or enhancers not "naturally occurring," i.e., containing different elements of different transcriptional regulatory regions, and/or mutations that alter expression.

It may be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression. The promoters employed may be constitutive, tissue-specific, inducible, and/or useful under the appropriate conditions to direct high-level expression of the introduced DNA segment, such as is advantageous in the large-scale production of recombinant proteins and/or peptides. The promoter may be heterologous or endogenous. Surprisingly, we found that simultaneous inclusion of both a CMV promoter/enhancer upstream of an E1A delta-24 region and a SV40 promoter/enhancer in the partially-deleted region of E3 region imparted a dramatic increase in tumor-specific viral replication and tumor-specific oncolysis of at least 10 to 100 fold better compared to control viruses that lacked the dual promoter feature.

Methods of Screening Adenoviruses for Therapeutic Utility

Oncolytic adenoviruses of the disclosure, or variants or derivatives thereof, can be evaluated for their therapeutic utility by examination of their lytic potential in tumor cells. The tumor cells may include primary tumor cells derived from patient biopsies or surgical resections. Alternatively, the tumor cells may include tumor cell lines. The cytolytic activity of adenoviruses of the disclosure can be determined in tumor cell lines in vitro by infection of cells with serial dilutions of adenovirus and determining the cytolytic potency (i.e. $IC_{50}$). Particular methods for determining cytolytic activity may include but are not limited MTS, MTT, and ATP colorimetric assays. Real time cellular cytotoxicity assays may also be used for determining cytolytic activity.

The therapeutic index, a comparison of the amount of a therapeutic agent that causes the therapeutic effect to the amount that causes toxicity, of an oncolytic adenovirus of the disclosure may be calculated by comparing the potency of the cytolytic potency of the adenovirus in a tumor cell line with the cytolytic potency in a matched normal cell.

Figure 3:
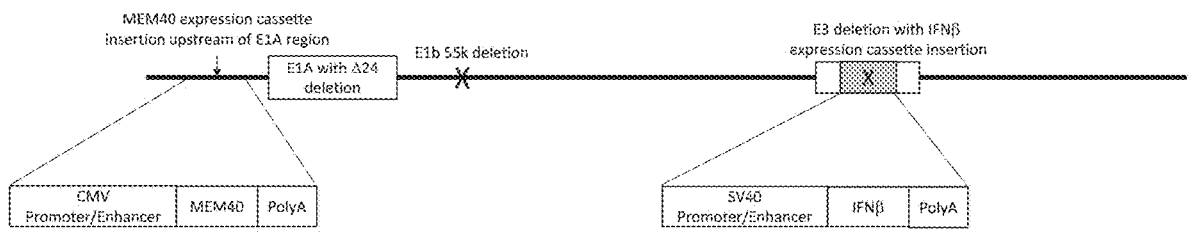
FIG. 3 schematically shows a replication-enhanced oncolytic adenovirus (MEM-288) encoding two transgenes: chimeric CD40 ligand (MEM40) and IFN-beta (IFNβ).

The oncolytic adenoviruses of the disclosure can be further evaluated for therapeutic utility by evaluation of their ability to infect tumor cells and/or normal cells and express a functional protein(s) encoded by the oncolytic adenovirus. One example of the present invention is a replication-enhanced oncolytic virus (MEM-288) encoding both a chimeric CD40 ligand (MEM40) under control of the CMV promoter/enhancer and IFNβ under control of the SV40 early promoter/enhancer (FIG. 3). These proteins can be detected by antibodies that specifically recognize each protein expressed by cells following infection with MEM-288. The nucleic acid sequence of the chimeric CD40 ligand (MEM40) was described as ISF35 in U.S. Pat. No. 7,495,090, which is herein incorporated by reference.

The oncolytic adenoviruses of the disclosure can further be evaluated for their ability to target tumor cell growth and the capacity to reduce tumorigenesis or tumor cell burden in mice harboring naturally derived or transplanted tumors in syngeneic or xenogeneic tumor models in mice. Tumor burden as measured by tumor size, immune protection from tumor rechallenge, and animal survival are all possible measures of therapeutic utility and animal tumor models.

Methods of Treatment and Administration

Within various embodiments of the disclosure, methods are also provided for treating cancer, comprising administering to a subject having cancer the adenovirus as described herein. An oncolytic adenovirus of the present invention may be administered by intratumoral injection. However, other routes of delivery may also be considered, including intravenously, intraperitoneally, intratracheally, intramuscularly, intracranially, endoscopically, intralesionally, percutaneously, subcutaneously, regionally, or by direct injection or perfusion.

Within particular embodiments, the cancer is treated utilizing a composition (e.g., a pharmaceutical composition) as described herein. As noted above, the term "cancer" as utilized herein refers to a large family of diseases characterized by the uncontrolled growth of cells in a body. Representative forms of cancer include carcinomas, sarcomas, myelomas, leukemias, lymphomas, and mixed types of the above. Further examples include, but are not limited to bile duct cancer, bladder cancer, brain cancers such as glioblastomas, breast cancer, cervical cancer, CNS tumors (such as a glioblastoma, astrocytoma, medulloblastoma, craniopharyogioma, ependymoma, pinealoma, hemangioblastoma, acoustic neuroma, oligodendroglioma, menangioma, neuroblastoma and retinoblastomas), colorectal cancer, endometrial cancer, hematopoietic cell cancers including leukemias and lymphomas, hepatocellular cancer, kidney cancer, laryngeal cancer, lung cancer, melanoma, oral cancer, ovarian cancer, pancreatic cancer, prostate cancer, squamous cell carcinoma, and thyroid cancer. Cancers may be diffuse (e.g., leukemias), comprise solid tumors (e.g., sarcomas such as fibrosarcoma, myxosarcoma, liposarcoma, chondrosarcoma and osteogenic sarcoma), or some combination of these (e.g., a metastatic cancer having both solid tumors and disseminated or diffuse cancer cells). For example, any cancer patient eligible to receive an autologous or allogeneic stem cell transplant would be considered to be a candidate for this therapy.

In some embodiments, administration can be accomplished by direct administration to a tumor, or to the former site of a tumor (e.g., after surgical resection or an ablation therapy). Administration can be made by direct injection, or by infusion over a selected period of time.

Direct injection into a tumor (intratumoral injection) can be accomplished by a fine catheter or cannula. With certain embodiments, the pharmaceutical compositions provided herein can be delivered by a microelectromechanical (MEMS) system under MR intra-procedural guidance.

When administered to a subject, an effective amount of a composition as described herein is given in order to treat (e.g., alleviate, improve, mitigate, ameliorate, stabilize, prevent the spread of, slow or delay the progression of or cure) a cancer. For example, it may be an amount sufficient to achieve the effect of reducing the number or destroying cancerous cells or neoplastic cells or by inhibiting the growth and/or proliferation of such cells. In order to be clinically effective, a composition(s) as provided herein could be given once, or, multiple times, depending on the treatment regimen.

A regimen for treatment using the replication-enhanced oncolytic adenovirus of the present invention may comprise a single administration or multiple administrations. Multiple administrations may be performed on a recurring schedule and/or in response to one or more indicators of efficacy of one or more prior administrations, or side effects of one or more prior administrations, among others that will be apparent to the person of ordinary skill in the art having the benefit of the present disclosure.

The dose of the pharmaceutical composition that is to be used can depend on the particular condition being treated, the severity of the condition, the individual patient parameters including age, physical condition, size and weight, the duration of the treatment, the nature of concurrent therapy (if any), the specific route of administration and other similar factors that are within the knowledge and expertise of the health practitioner. In addition, the dosage may depend on the availability of product.

EXAMPLES

Example 1. Dual Promoter Replication-Enhanced Oncolytic Adenoviruses

A template replication-enhanced oncolytic adenovirus type 5 (FIG. 1) is shown with the following features: a CMV promoter/enhancer represented by SEQ ID NO: 1 and a SV40 promoter/enhancer represented by SEQ ID NO: 2. A preferred embodiment of this generalized vector construct further shown (FIG. 2) with the following features: a CMV promoter/enhancer represented by SEQ ID NO: 1 downstream of the left inverted terminal repeat (ITR) and upstream of the functional E1A region; a SV40 promoter/enhancer represented by SEQ ID NO: 2 in the E3 region; a E1A gene region containing a 24 nucleotide deletion; a partial or complete deletion of the E3 region; and a deletion of the E1b 55k region. This template replication-enhanced oncolytic virus is capable of further modifications including addition of heterologous nucleic acids downstream of either the CMV promoter/enhancer or SV40 promoter/enhancer for expression of therapeutic protein(s).

Figure 4:
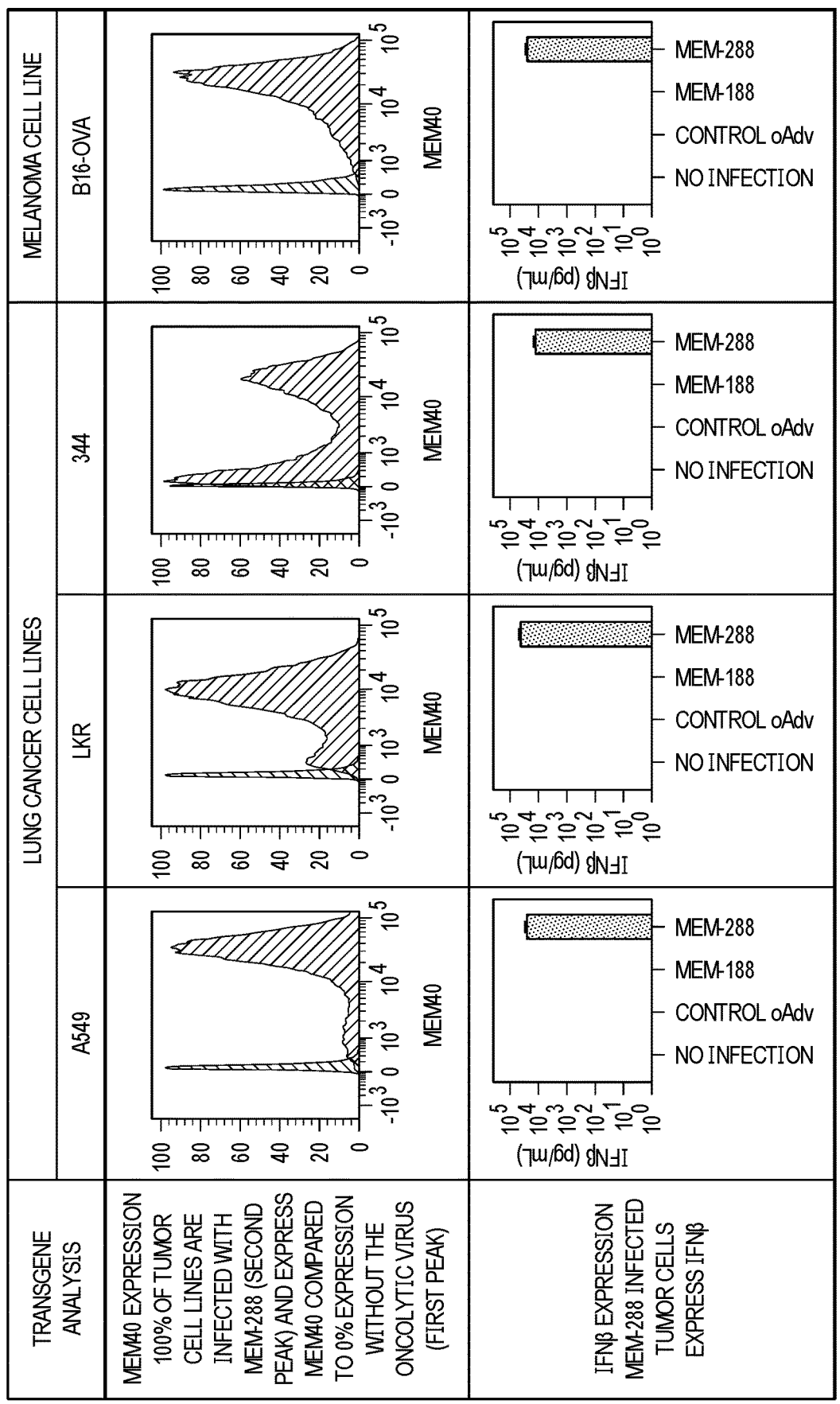
FIG. 4 shows dual transgene expression by different tumor cells following infection with a replication-enhanced oncolytic adenovirus (MEM-288) encoding two transgenes (MEM40 and IFNβ). In vitro expression of MEM40 (flow cytometry) and IFNβ (ELISA) were determined following infection at multiplicity of infection (MOI)=250 for 2 days. IFNβ results also show comparison of transgene expression by MEM-288 compared to MEM-188 armed only with MEM40 or control oncolytic adenovirus (Control oAdv) armed with only GFP reporter transgene under control of the CMV promoter/enhancer region and lacking the SV40 promoter/enhancer.
Figure 5:
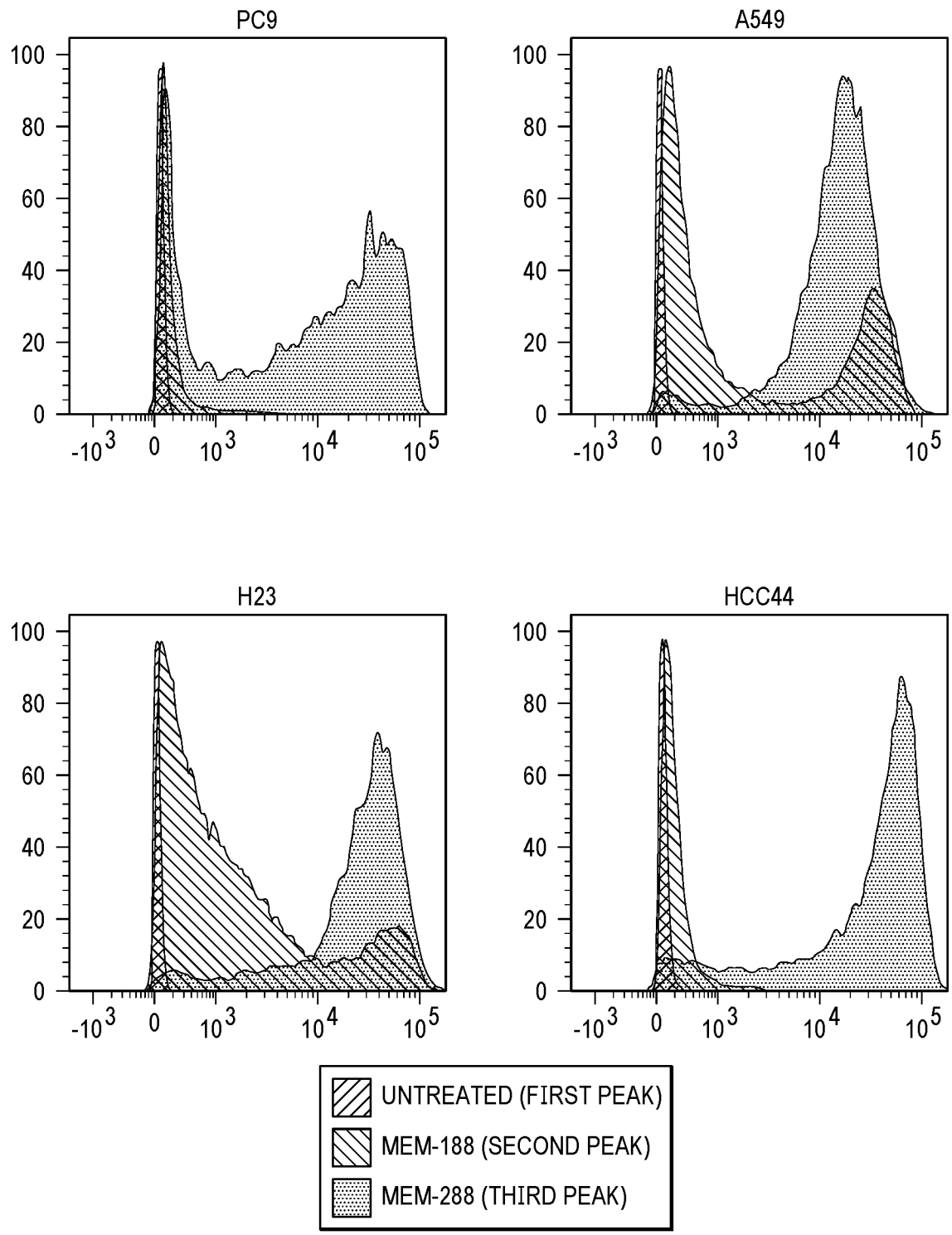
FIG. 5 shows chimeric CD40 ligand (MEM40) expression on different tumor cell lines following infection with either MEM-188 or MEM-288.

Example 2. Construction of a Dual Promoter Replication-Enhanced Oncolytic Adenovirus Encoding Two Transgenes A replication-enhanced oncolytic adenovirus type 5 (FIG. 3) was constructed with the following features: a CMV promoter/enhancer represented by SEQ ID NO: 1 downstream of the left inverted terminal repeat (ITR) and upstream of the functional E1A region; a SV40 promoter/enhancer represented by SEQ ID NO: 2 in the E3 region; a EIA gene region containing a 24 nucleotide deletion; a partial or complete deletion of the E3 region; and a deletion of the E1b 55k region. In addition, heterologous nucleic acids encoding a chimeric CD40 ligand (MEM40) cloned downstream of the CMV promoter/enhancer and IFNβ cloned downstream of the SV40 promoter/enhancer were incorporated. This replication-enhanced oncolytic adenovirus is called MEM-288 and is capable of expression of two proteins that can be readily expressed and detected from tumor cells following infection (FIG. 4). We also directly compared expression of MEM40 on tumor cells following infection at equivalent infectious titer with either MEM-288 or a similar oncolytic adenovirus vector (MEM-188) that contains the heterologous nucleic acid encoding a chimeric CD40 ligand (MEM40) cloned downstream of the CMV promoter/enhancer but does not contain the SV40 promoter/enhancer and IFNβ transgene inserts. MEM-288 expressed higher levels of the MEM40 transgene versus MEM-188 across a panel of different lung tumor types (FIG. 5).

Example 3. Enhanced Viral Replication in Tumor Cells

Figure 6:
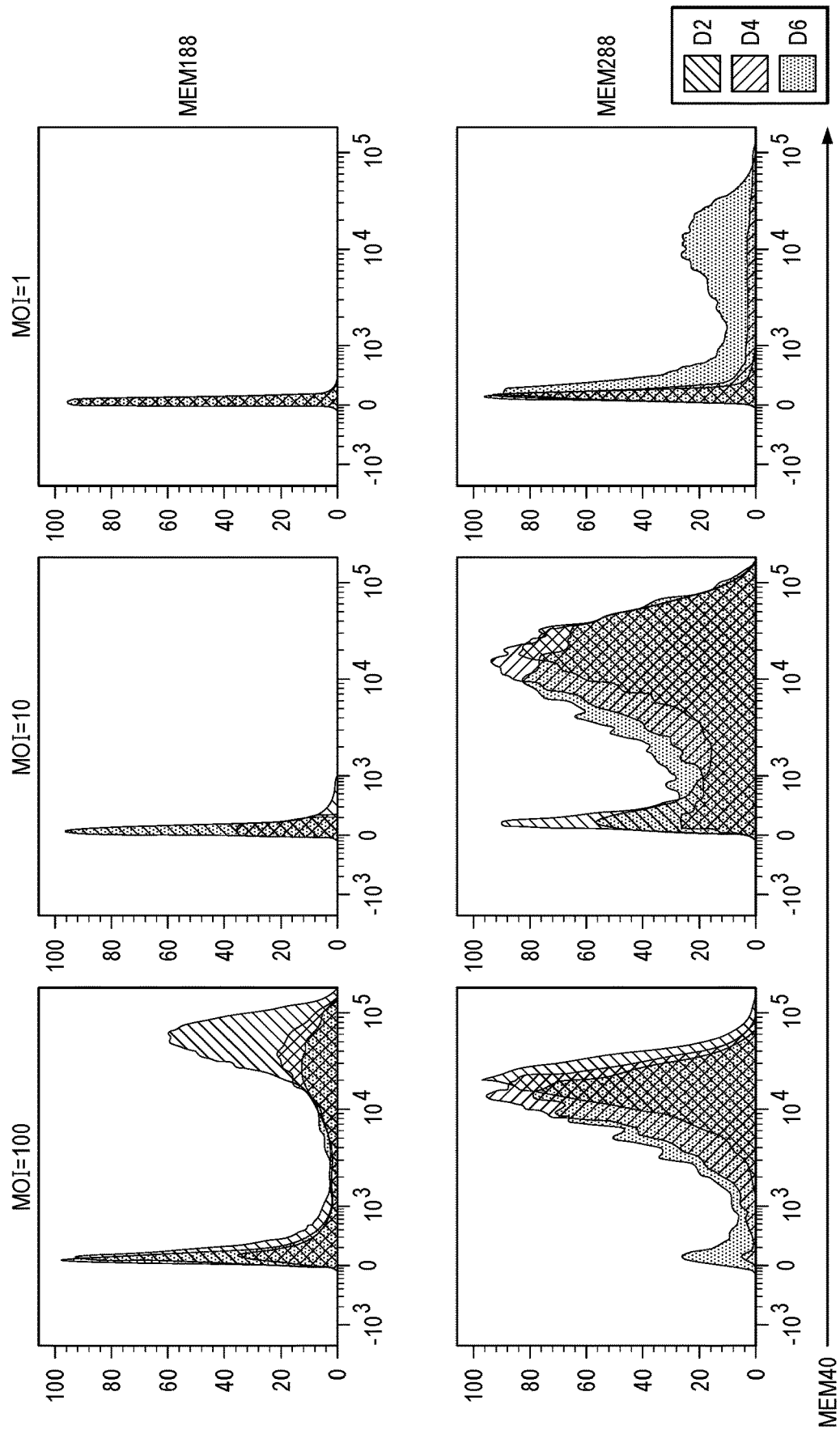
FIG. 6 shows dose and time-dependent expression of MEM40 on A549 lung tumor cells following infection with either MEM-188 or MEM-288.
Figure 7:
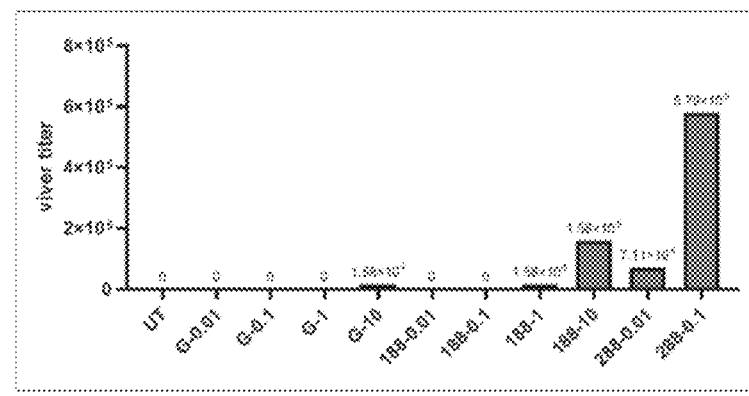
FIG. 7 shows virus titer from A549 cells infected with Ad-GFP (G), MEM-188 (188) and MEM-288 (288) at the indicated Multiplicity of Infection (MOI). After freeze-thaw lysis, released infectious virus levels were determined following infection of AD-293 cells using the QuickTiter™ Adenovirus Titer Immunoassay Kit.

A549 tumor cells were infected with increasing titers of MEM-288, a replication-enhanced oncolytic adenovirus containing the dual CMV and SV40 promoter/enhancer elements (FIG. 6). Direct comparisons were made to control viruses (Ad-GFP and MEM-188) with similar feature-sets with the exception they lack the SV40 promoter/enhancer element. MEM-288 resulted in greatly increased MEM40 expression, which was especially noticeable at MOI 10 and MOI 1. At MOI 1, where MEM-188 showed no transgene expression, MEM-288 showed increase MEM40 expression over time to become especially pronounced on day 6 after infection. These findings indicate greater replication ability of MEM-288. To more directly determine whether MEM-288 replicated more proficiently, we performed a standard replication assay based on release of intracellular virus by freeze-thaw lysis. A549 cells were infected with Ad-GFP, MEM-188 and MEM-288 at different MOI following which intracellular levels of viruses were determined 2 days later using 293 cells to calculate infectious virus titer using a hexon staining kit from Cell Biolabs, Inc. Ad-GFP infection of A549 produced detectable levels of virus replication starting at an MOI of 10 (FIG. 7). MEM-188 virus produced detectable virus replication starting at MOI of 1. In contrast, even an MOI 0.01 and MOI of 0.1 of MEM-288 led to high level virus replication; furthermore, infection with MOI of 1 or higher of MEM-288 led to a hexon staining signal which was too high for quantitation. These results indicate that the replication ability of MEM-288 is likely >100-1000 fold higher than the other viruses tested lacking the dual promoter/enhancer elements of this invention.

Figure 8:
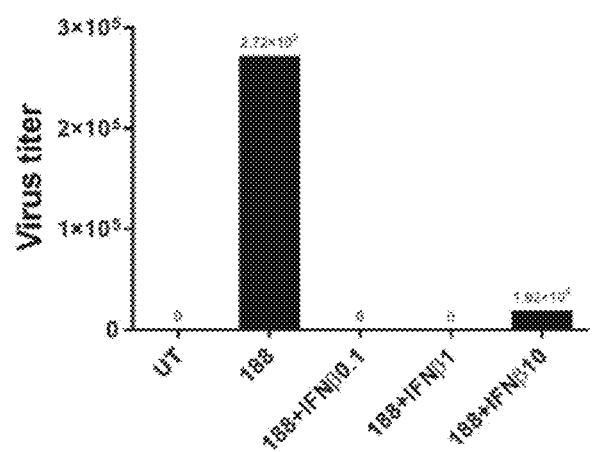
FIG. 8 shows virus titer from A549 cells infected MEM-188 (188) at MOI of 10 with addition of exogenous recombinant IFNβ protein. After freeze-thaw lysis, released infectious virus levels were determined following infection of AD-293 cells using the QuickTiter™ Adenovirus Titer Immunoassay Kit.
Figure 9:
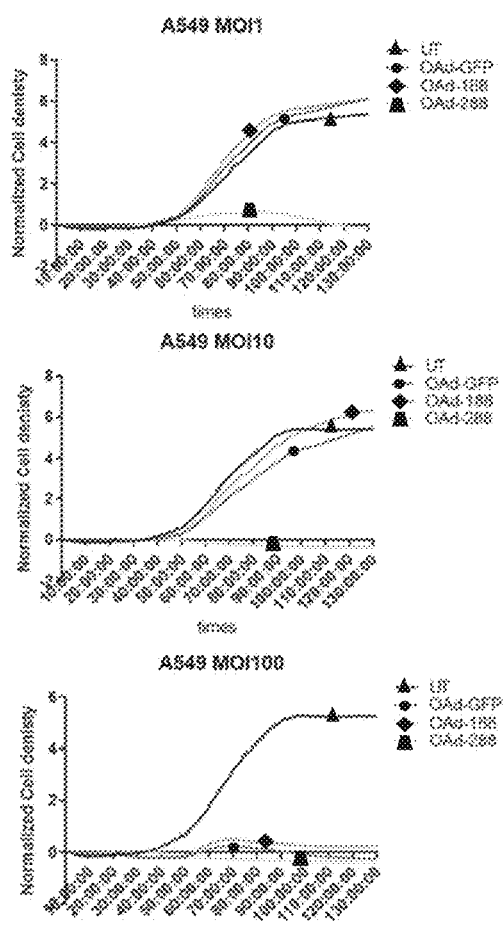
FIG. 9 shows enhanced oncolytic activity of MEM-288 containing both CMV promoter/enhancer and SV40 promoter/enhancer elements compared to control viruses with only a CMV promoter/enhancer element towards A549 tumor cells as determined by Real-Time Cell Analysis (RTCA) assay.
Figure 10:
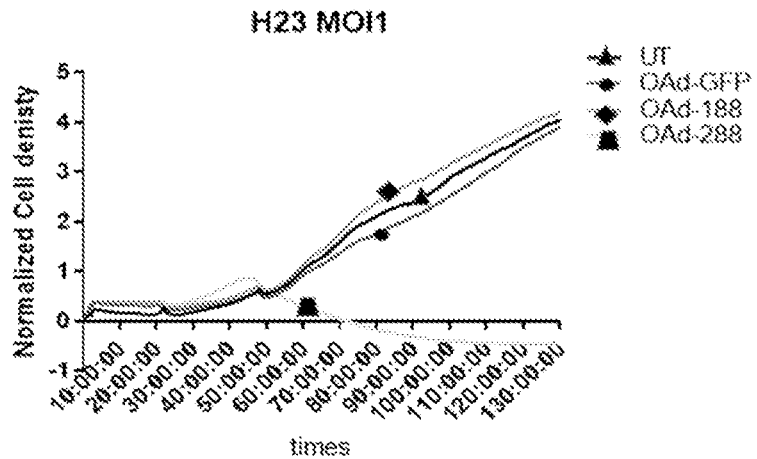
FIG. 10 shows enhanced oncolytic activity of MEM-288 containing both CMV promoter/enhancer and SV40 promoter/enhancer elements compared to control viruses with only a CMV promoter/enhancer element towards H23 tumor cells as determined by Real-Time Cell Analysis (RTCA) assay.
Figure 10:
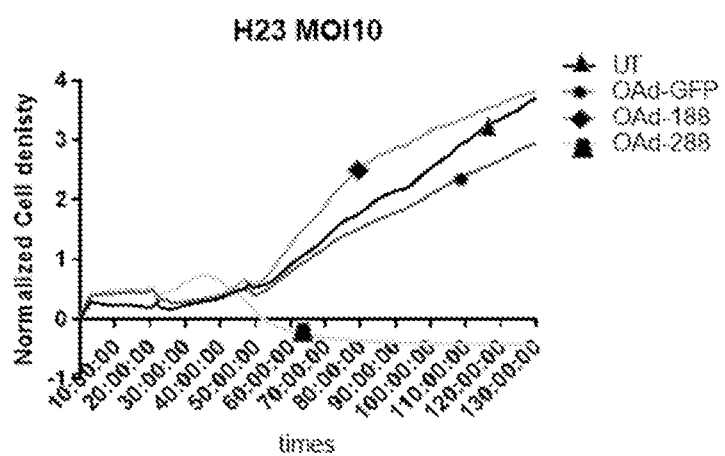
Figure 10:
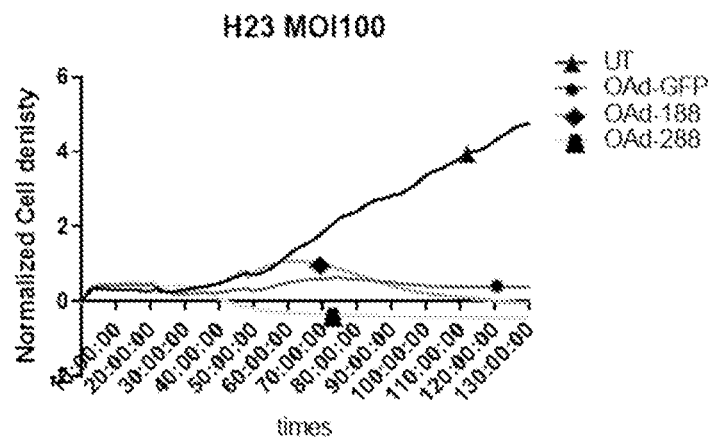
Figure 11:
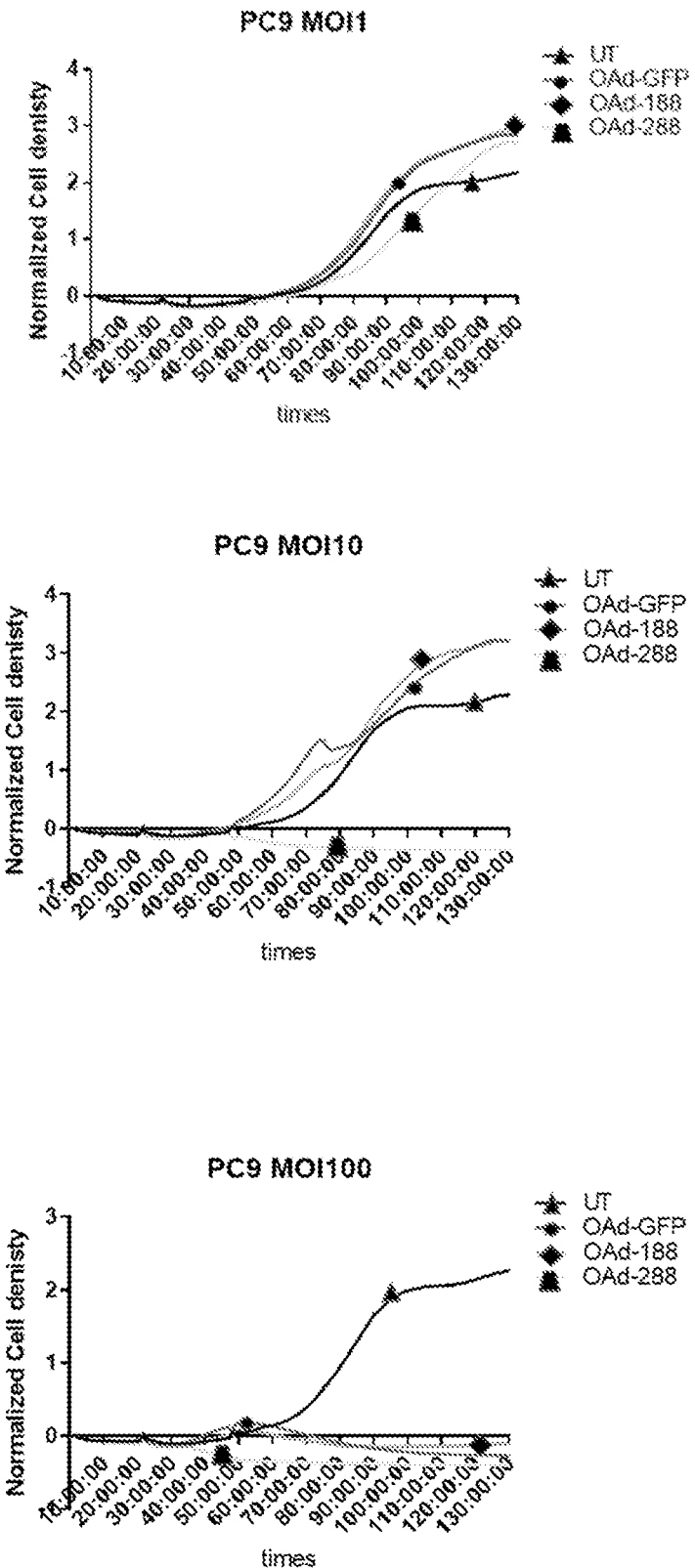
FIG. 11 shows enhanced oncolytic activity of MEM-288 containing both CMV promoter/enhancer and SV40 promoter/enhancer elements compared to control viruses with only a CMV promoter/enhancer element towards PC9 tumor cells as determined by Real-Time Cell Analysis (RTCA) assay.
Figure 12:
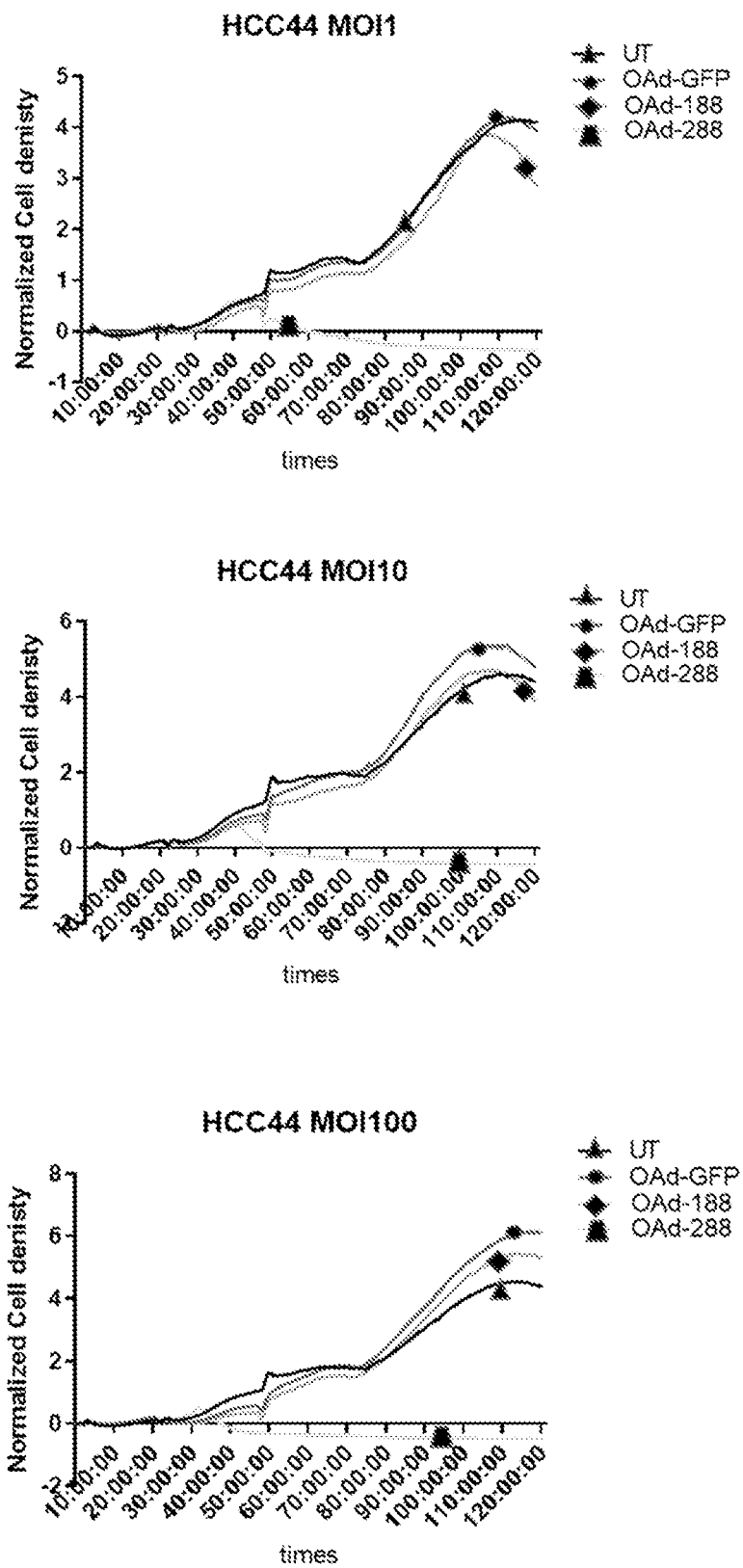
FIG. 12 shows enhanced oncolytic activity of MEM-288 containing both CMV promoter/enhancer and SV40 promoter/enhancer elements compared to control viruses with only a CMV promoter/enhancer element towards HCC44 tumor cells as determined by Real-Time Cell Analysis (RTCA) assay.

MEM-288 is different from MEM-188 in having an SV40 promoter/enhancer and an IFNβ transgene. To determine if either the SV40 or the IFNβ elements were contributing to higher replication of MEM-288, we added recombinant human IFNβ to MEM-188 infected A549 following which virus replication was determined as described above. Importantly, IFNβ addition did not increase replication but instead decreased it by a factor of ~14 (FIG. 8). This result suggests that SV40 promoter/enhancer in E3 region mediates increased oncolytic effect and replication of MEM-288.

Example 4. Enhanced Oncolytic Activity

We infected A549 lung tumor cells with Ad-GFP, MEM-188 or MEM-288 at different multiplicity of infection (MOI) following which viable cell numbers were determined. These analyses were further expanded in additional cell lines and by additional methods for determining oncolysis, including use of an impedance-based system (xCELLigence system) which permits highly accurate measurements of cancer cell viability based on adherence to plates over time. This Real-Time Cell Analysis (RTCA) was conducted by plating tumor lines at a density of 2,500 cells per well and allowing to attach overnight. Oncolytic virus was added to the cultures and cancer cell viability measurements were taken every 15 minutes for up to 120 hours. In studies with 4 lung cell lines, A549, H23, PC9, and HCC44 (FIGS. 9-12, respectively), we again found increased oncolytic activity by 10 to 100-fold for MEM-288.

Figure 13:
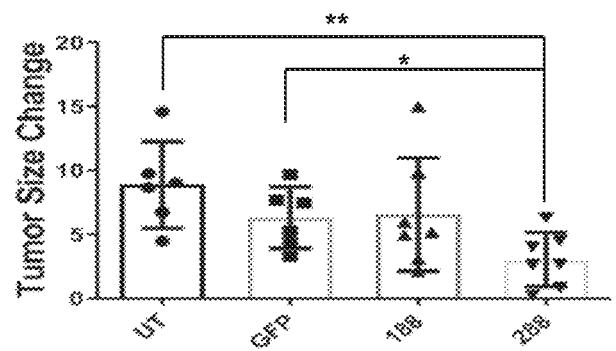
FIG. 13 shows change in A549 luciferase expressing tumor implanted in SCID mice and intratumorally injected Ad-GFP, MEM-188, or MEM-288. Viable tumor is shown on D14 after the first virus injection compared to the baseline before treatment.

We next used SCID mice bearing s.c. A549 tumors expressing firefly luciferase, which allowed quantification of live tumor cells. Following 2 injections of the 3 different viruses (10e9 infectious units/injection), MEM-288 significantly reduced tumor growth compared to Ad-GFP and MEM-188 (FIG. 13). These results indicate that the higher oncolytic effect of MEM-288 is also evident in vivo.

Example 5. Enhanced Oncolytic Activity and Tumor Specificity

Figure 14:
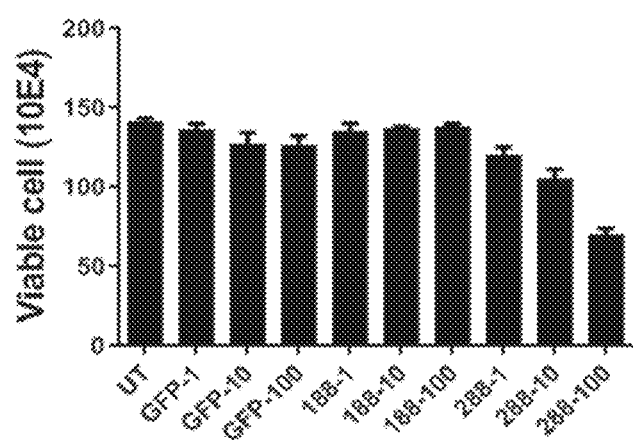
FIG. 14 shows viability of Raji human B cell lymphoma cells following infection with Ad-GFP, MEM-188, or MEM-288.

Lymphoid tumor cells resist lysis by oncolytic viruses, including oncolytic adenovirus. Human B-cell tumor cell line Raji was used to determine potential effect of MEM-288 on cell viability. Control Ad-GFP and MEM-188 did not show loss of cell viability up to an MOI of 100 (FIG. 14). In contrast a clear dose-dependent loss of Raji cell viability was observed following infection with MEM-288 (FIG. 14).

Figure 15:
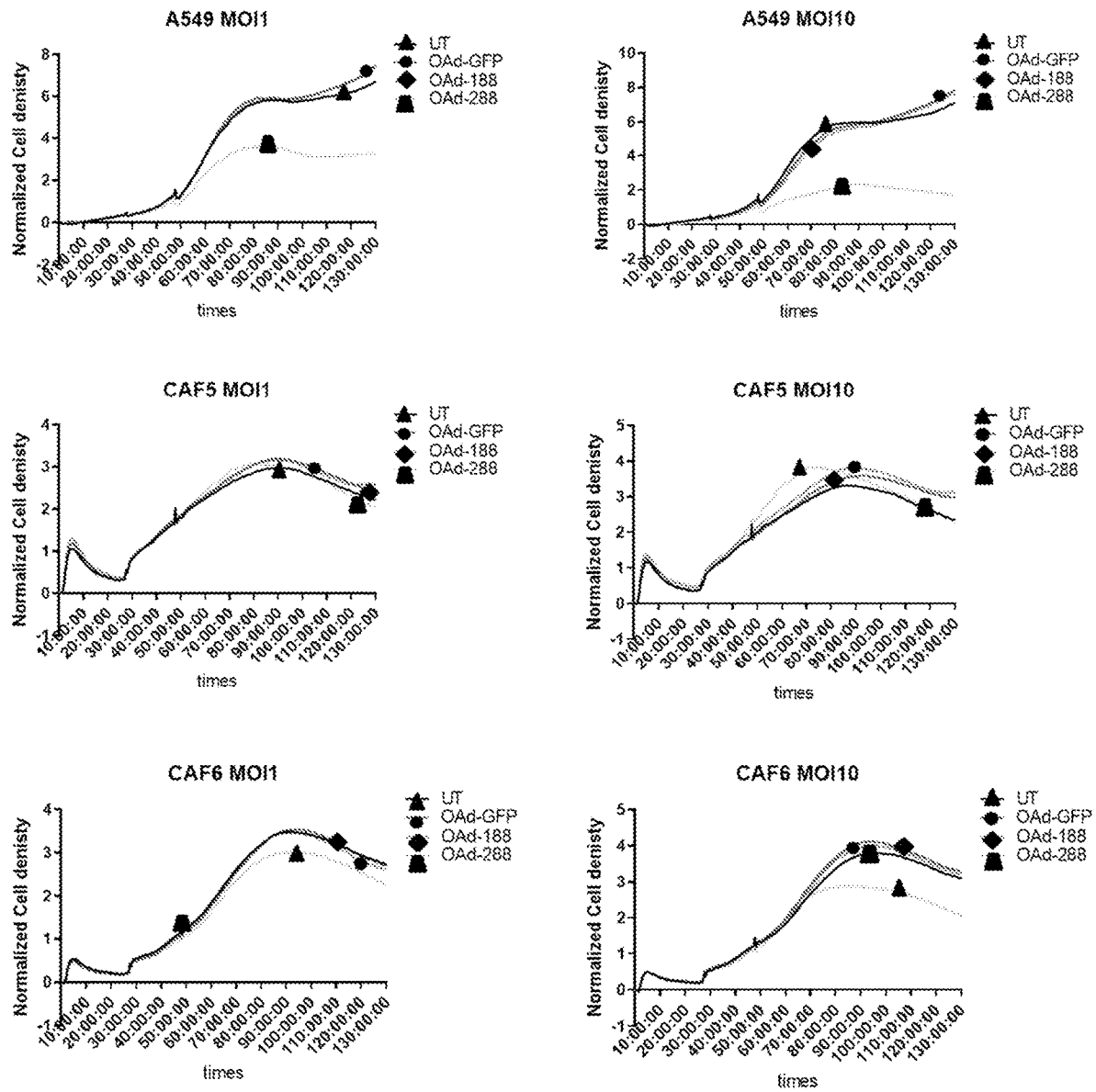
FIG. 15 shows tumor-specific oncolytic activity of MEM-288, MEM-188, and Ad-GFP oncolytic viruses following infection of A549 tumor cells and cancer associated fibroblast cell (CAF) isolates as determined by Real-Time Cell Analysis (RTCA) assay.

Critically, this oncolytic effect was specific for tumor cells since we also found that significant killing was not observed in non-cancerous cells such as human lung cancer associated fibroblasts (CAFs) (FIG. 15). While MEM-288 had a notable oncolytic effect at MOI 1 and MOI 10 using the RTCA assay, two independently derived CAF isolates did not show such a clear oncolytic effect (FIG. 15).

Figure 16:
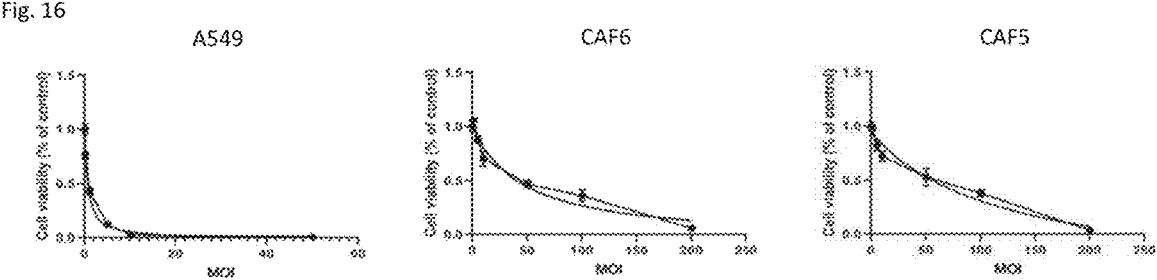
FIG. 16 shows dose-titration tumor-specific oncolytic activity of MEM-288 in A549 tumor cells in comparison to oncolytic activity in cancer associated fibroblast cell (CAF) isolates as determined by Real-Time Cell Analysis (RTCA) assay.

Using a wide range of MOI, we next determined the potential fold difference between A549 tumor cells and CAFs (FIG. 16). Comparing the infectious dose level resulting in 50% death of cells (IC50), we found an IC50 of 0.73 for A549 tumor cells versus IC50s of 45.2 and 122.9 for two independently derived CAF isolates. These results translate into 61.9 and 168.3 fold differences, respectively, in ability of MEM-288 to induce lysis of cancer versus normal cells (FIG. 16).

Figure 17:
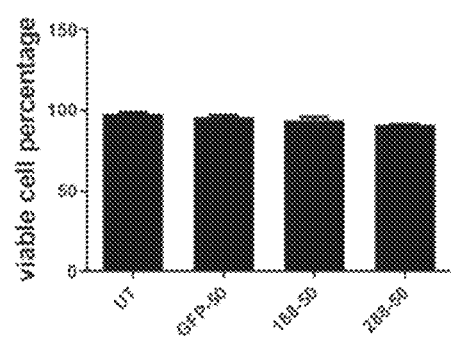
FIG. 17 shows cell viability as a percentage of untreated (UT) human monocyte-derived dendritic cells infected with Ad-GFP, MEM-188 and MEM-288 at an MOI of 50 for 2 days.

While CAFs undergo robust growth (i.e. cell division) in vitro, we also determined MEM-288 oncolytic effects on non-dividing human monocyte-derived dendritic cells (DCs). Infection at a high MOI of 50, which typically completely eradicates tumor cells, did not impact the viability of DCs after infection with MEM-288 or the control viruses (FIG. 17). These results indicate the tumor cell specificity of this innovative replication-enhanced oncolytic adenovirus.

Example 6. Enhanced Oncolytic Activity not Affected by Adenovirus E3 Regulatory Domains As previously described, modulation of the biological properties of oncolytic adenoviruses can impact a range of immune interactions that may be beneficial or detrimental in effect on cancer treatment. The interactions depend on the specific tumor, the site and extent of the disease, the immunosuppressive tumor microenvironment, the oncolytic virus platform, the dose, time, and delivery conditions, as well as individual patient responses (see generally Aurelian L., "Oncolytic viruses as immunotherapy: progress and remaining challenges," Onco. Targets Ther. 2016, 9:2627-2637). For example, the presence of adenovirus E3 genes has been reported to increase the oncolytic potency of conditionally replicating adenovirus in vitro and in vivo (see Suzuki K, Alemany R, Yamamoto M, and Curiel D T, "The presence of the adenovirus E3 region improves the oncolytic potency of conditionally replicative adenoviruses" Clin. Cancer Res. 2002 Nov., 8(11):3348-59). In particular, the E3-11.6 kDa Adenovirus Death Protein (ADP) is thought to be required for efficient cell death (see Tollefson A, Ryerse J, and Scaria A, et al. "The E3-11.6-kDa Adenovirus Death Protein (ADP) is Required for Efficient Cell Death: Characterization of Cells Infected with adp Mutants," Virology 1996, 220:152-162).

We examined the potential contribution of E3 adenovirus regions in our oncolytic adenovirus by examining two different control GFP-encoding oncolytic adenoviruses, one GFP virus containing an almost complete E3 deletion as described in FIGS. 4, 7, 9-17 and another GFP virus (Ad-GFP-2) containing a partial E3 deletion set (E3 6.7k and E3 19k deletions) found in MEM-288.

Figure 18:
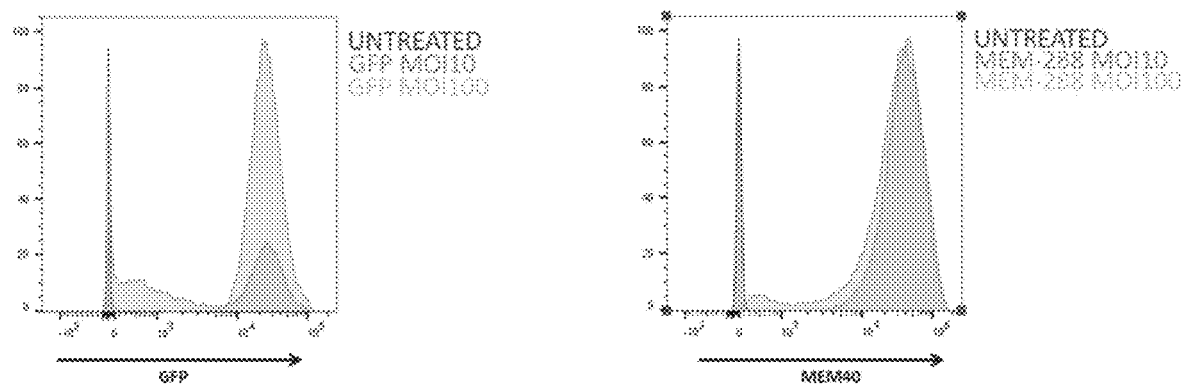
FIG. 18 shows GFP or chimeric CD40 ligand (MEM40) expression in A549 human lung cancer cell line following infection with either a replication-enhanced oncolytic adenovirus containing the same E3 adenovirus regional deletions (E3 6.7k and E3 19k deletions) found in MEM-288 and also encoding the GFP transgene (GFP; Ad-GFP-2) or MEM-288 oncolytic adenovirus, respectively. For comparison, this Ad-GFP-2 construct is different from the Ad-GFP control virus construct described in FIGS. 4, 7, 9-17 that contains almost complete E3 regional deletion. Panel (A) shows GFP expression in uninfected cells (untreated) or cells infected at MOI 10 and 100 with Ad-GFP-2. Panel (B) shows MEM40 expression in uninfected cells (untreated) or cells infected at MOI 10 and 100 with MEM-288. This result indicates that at a lower MOI of 10, MEM-288 leads to a higher proportion of cells with MEM40 than Ad-GFP-2 suggesting potentially greater replication of MEM-288 versus Ad-GFP-2.

FIG. 18 shows GFP or chimeric CD40 ligand (MEM40) expression in A549 human lung cancer cell line following infection with either Ad-GFP-2 or MEM-288. Panel (A) shows GFP expression in uninfected cells (untreated) or cells infected at MOI 10 and 100 with Ad-GFP-2. Panel (B) shows MEM40 expression in uninfected cells (untreated) or cells infected at MOI 10 and 100 with MEM-288. This result indicates that at a lower MOI of 10, MEM-288 leads to a higher proportion of cells with MEM40 than Ad-GFP-2 suggesting potentially greater replication of MEM-288 versus Ad-GFP-2.

Figure 19:
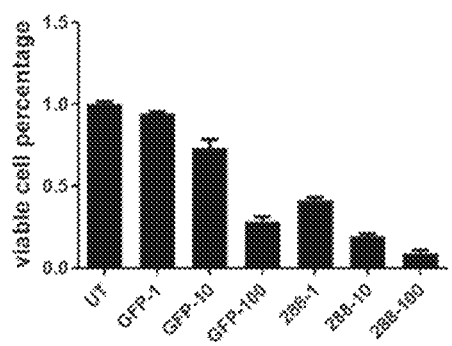
FIG. 19 shows viability of A549 human lung cancer cell line following infection with Ad-GFP-2 or MEM-288. Ad-GFP-2 and MEM-288 were used to infect cells at indicated MOI of 1, 10 and 100. 2 days later, remaining viable cells were counted and are shown as a percentage of untreated cells (UT). This result indicates greater oncolytic activity of MEM-288 in comparison with Ad-GFP-2 at all 3 MOIs. Therefore, greater oncolytic activity of MEM-288 is not primarily driven by the type of E3 deletion, but instead was unexpectedly highly-dependent on inclusion of the SV40 promoter in the E3 region.

FIG. 19 shows viability of A549 human lung cancer cell line following infection with Ad-GFP-2 or MEM-288. Ad-GFP-2 and MEM-288 were used to infect cells at indicated MOI of 1, 10 and 100. 2 days later, remaining viable cells were counted and are shown as a percentage of untreated cells (UT). This result indicates greater oncolytic activity of MEM-288 in comparison with Ad-GFP-2 at all 3 MOIs. Furthermore, these results mirror the results of MEM-288 versus the GFP control virus containing an almost complete E3 regional deletion as described in FIGS. 4,7,9-17.

These results in total thus indicate our innovative replication-enhanced adenovirus vector possesses greater viral replication and oncolytic activity for the most part independent of any E3 regional contributions, including in-part or total E3 deletions, that would not be obvious to those skilled in the art based on prior art described in the references above.

The particular embodiments disclosed above are illustrative only, as the disclosure may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the disclosure. Accordingly, the protection sought herein is as set forth in the claims below.

What is claimed is:

1. An adenovirus vector, wherein the adenovirus vector comprises:
   a. a CMV promoter/enhancer inserted in a noncoding region upstream of the adenovirus E1 coding region;
   b. a SV40 promoter/enhancer inserted in the adenovirus E3 region;
   c. a deletion in part or all of the E3 coding region;
   d. a E1A gene comprising a delta-24 deletion;
   e. a E1B 55K deletion;
   f. wherein the CMV promoter/enhancer is operably linked to a heterologous nucleic acid sequence encoding MEM40; and
   g. wherein the SV40 promoter/enhancer is operably linked to a heterologous nucleic acid sequence encoding IFNβ.

2. The adenovirus vector of claim 1, wherein the adenovirus is serotype 5.

3. The adenovirus vector of claim 1, wherein the CMV promoter/enhancer is located between the left inverted terminal repeat (ITR) and 5'-end of the functional E1A region.

4. The adenovirus vector of claim 1, wherein the SV40 promoter/enhancer is located between the E3 12.5K and E3 RID-alpha regions.

5. The adenovirus vector of claim 1, wherein
   a. the CMV promoter/enhancer comprises the nucleotide sequence of SEQ ID NO: 1; and
   b. the SV40 promoter/enhancer comprises the nucleotide sequence of SEQ ID NO: 2.

6. The adenovirus vector of claim 1, wherein the CMV promoter/enhancer comprises the nucleotide sequence of SEQ ID NO: 1.

7. The adenovirus vector of claim 1, wherein the SV40 promoter/enhancer comprises the nucleotide sequence of SEQ ID NO: 2.

* * * * *

SEQUENCE LISTING

```
<160> NUMBER OF SEQ ID NOS: 2

<210> SEQ ID NO 1
<211> LENGTH: 617
<212> TYPE: DNA
<213> ORGANISM: Artificial Sequence
<220> FEATURE:
<223> OTHER INFORMATION: CMV Promoter/Enhancer

<400> SEQUENCE: 1
acattgatta ttgactagtt attaatagta atcaattacg gggtcattag ttcatagccc      60
atatatggag ttccgcgtta cataacttac ggtaaatggc ccgcctggct gaccgcccaa     120
cgacccccgc ccattgacgt caataatgac gtatgttccc atagtaacgc caatagggac     180
tttccattga cgtcaatggg tggagtattt acggtaaact gcccacttgg cagtacatca     240
agtgtatcat atgccaagta cgccccctat tgacgtcaat gacggtaaat ggcccgcctg     300
gcattatgcc cagtacatga cctatggga ctttcctact tggcagtaca tctacgtatt      360
agtcatcgct attaccatgg tgatgcggtt ttggcagtac atcaatgggc gtggatagcg     420
gtttgactca cggggatttc caagtctcca ccccattgac gtcaatggga gtttgttttg     480
gcaccaaaat caacgggact ttccaaaatg tcgtaacaac tccgccccat tgacgcaaat     540
gggcggtagg cgtgtacggt gggaggtcta tataagcaga gctctctggc taactagaga     600
acccactgct tactggc                                                    617
```

```
<210> SEQ ID NO 2
<211> LENGTH: 275
<212> TYPE: DNA
<213> ORGANISM: Artificial Sequence
<220> FEATURE:
<223> OTHER INFORMATION: SV40 Promoter/Enhancer

<400> SEQUENCE: 2
tgcatctcaa ttagtcagca accaggtgtg gaaagtcccc aggctcccca gcaggcagaa        60
gtatgcaaag catgcatctc aattagtcag caaccatagt cccgccccta actccgccca      120
tcccgcccct aactccgccc agttccgccc attctccgcc ccatggctga ctaattttt       180 ttatttatgc agaggccgag gccgcctcgg cctctgagct attccagaag tagtgaggag      240
gcttttttgg aggcctaggc ttttgcaaaa agctt                                 275
```